US00PP36241P2

(12) United States Plant Patent
Hansen

(10) Patent No.: US PP36,241 P2
(45) Date of Patent: Nov. 5, 2024

(54) ***DELOSPERMA* PLANT NAMED 'Pink Radiance'**

(50) Latin Name: ***Delosperma* hybrid**
Varietal Denomination: Pink Radiance

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,961

(22) Filed: Apr. 16, 2024

(51) Int. Cl.
*A01H 5/02* (2018.01)
*A01H 6/00* (2018.01)

(52) U.S. Cl.
USPC ..... Plt./422
CPC ..... *A01H 6/00* (2018.05)

(58) Field of Classification Search
USPC ..... Plt./422
CPC ..... A01H 5/02
See application file for complete search history.

*Primary Examiner* — Kent L Bell

(57) ABSTRACT

A new and distinct cultivar of *Delosperma* plant named 'Pink Radiance' is disclosed, characterized by abundant large flowers with petals of light lilac on the outside and rosy-purple on the inside nearly covering the plant. Plants have a low, mounding habit, and are tolerant to at least USDA zone 6. The new plant is useful for its bright flowers and low habit in the landscape or as a container plant.

2 Drawing Sheets

Latin name of the genus and species: *Delosperma* hybrid.
Variety denomination: 'Pink Radiance'.

STATEMENT REGARDING PRIOR DISCLOSURES UNDER 37 CFR 1.77 (b) (6)

The claimed plant was first sold or offered for sale by Walters Gardens, Inc. to Dallas Johnson Greenhouse, Inc. on Apr. 24, 2023, by Walters Gardens, Inc., who obtained the plant and all information relating thereto, from the inventor. Subsequently, on Dec. 1, 2023, the new plant was featured in a non-enabling disclosure of a brief description and photograph on a website operated by Walters Gardens, Inc. No plants of *Delosperma* 'Pink Radiance' have been sold in this country or anywhere in the world nor has any disclosure of the new plant been made more than one year prior to the filing date of this application, and such sale or disclosure within one year was either derived directly or indirectly from the inventor.

BACKGROUND OF THE INVENTION

The present invention relates to the new and distinct *Delosperma* cultivar named 'Pink Radiance' also referred to here as the new plant. 'Pink Radiance' was hybridized by the inventor at a wholesale perennial nursery in Zeeland, Michigan, USA as the result of a greenhouse cross between 'P001S' (not patented) as the female parent and 'Psfave' (not patented) as the male parent in the summer of 2019. Seeds from this pollination were collected in the fall of 2019 and were sown earlier the next year. The new plant originated as a single seedling, was initially evaluated in the summer of 2021, selected for further evaluation, and assigned the breeder code 19-7-1.

*Delosperma* 'Pink Radiance' has been successfully asexually propagated by shoot tip cuttings since 2021 at a wholesale perennial nursery in Zeeland, Michigan and found to produce identical stable and identical plants in successive generations of asexual propagation.

SUMMARY OF THE INVENTION

*Delosperma* 'Pink Radiance' differs from the parents as well as all other Hardy Ice Plant cultivars known to the inventor. The most similar known *Delosperma* cultivars include: 'Jewel of Desert Rosequartz' U.S. Plant Pat. No. 23,452, 'WOWDRW5' U.S. Plant Pat. No. 25,572, EARLY BIRD™ 'Purple' (not patented), 'Stardust' (not patented), 'Fig Fusion' U.S. U.S. Plant Pat. No. 31,343, and 'Orchid Flash' U.S. Plant patent application Ser. No. 18/445,962.

'Jewel of Desert Rosequartz' has fewer flowers per plant and the petals are more pinkish with a white base. 'WOWDRW5' has flower petals that are lighter magenta distally and the base is white. 'Purple' has purplish flower petals and the petal base is deeper magenta purple. 'Stardust' has a tighter clumping habit and flower petals with a pinkish-purple outer portion with a white center. 'Fig Fusion' has flower petals with a large white base. 'Orchid Flash' has deeper purple petals rather than the lighter lilac in the outer portion.

The female parent, 'P001S', has flower petals that are apricot to bright orange toward the outside with a ring of hot pink to magenta color surrounding the white eye. The male parent, 'Psfave', has petals that are light lavender on the outside with a smaller and lighter rosy-pink halo toward the middle.

*Delosperma* 'Pink Radiance' differs from the parents as well as all other Hardy Ice Plant cultivars known to the inventor. The following traits in combination have been repeatedly observed and are determined to be the unique characteristics of the new plant:

1. Low, mounded habit of small linear succulent foliage;
2. Winter hardy to at least USDA Zone 6 and drought and heat resistant;

3. Large flowers with petals of light lilac on the outside and rosy-purple on the inside;
4. Flowering on shoot tips and nodes;
5. Foliage takes on strong dark reddish color from late fall into spring.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
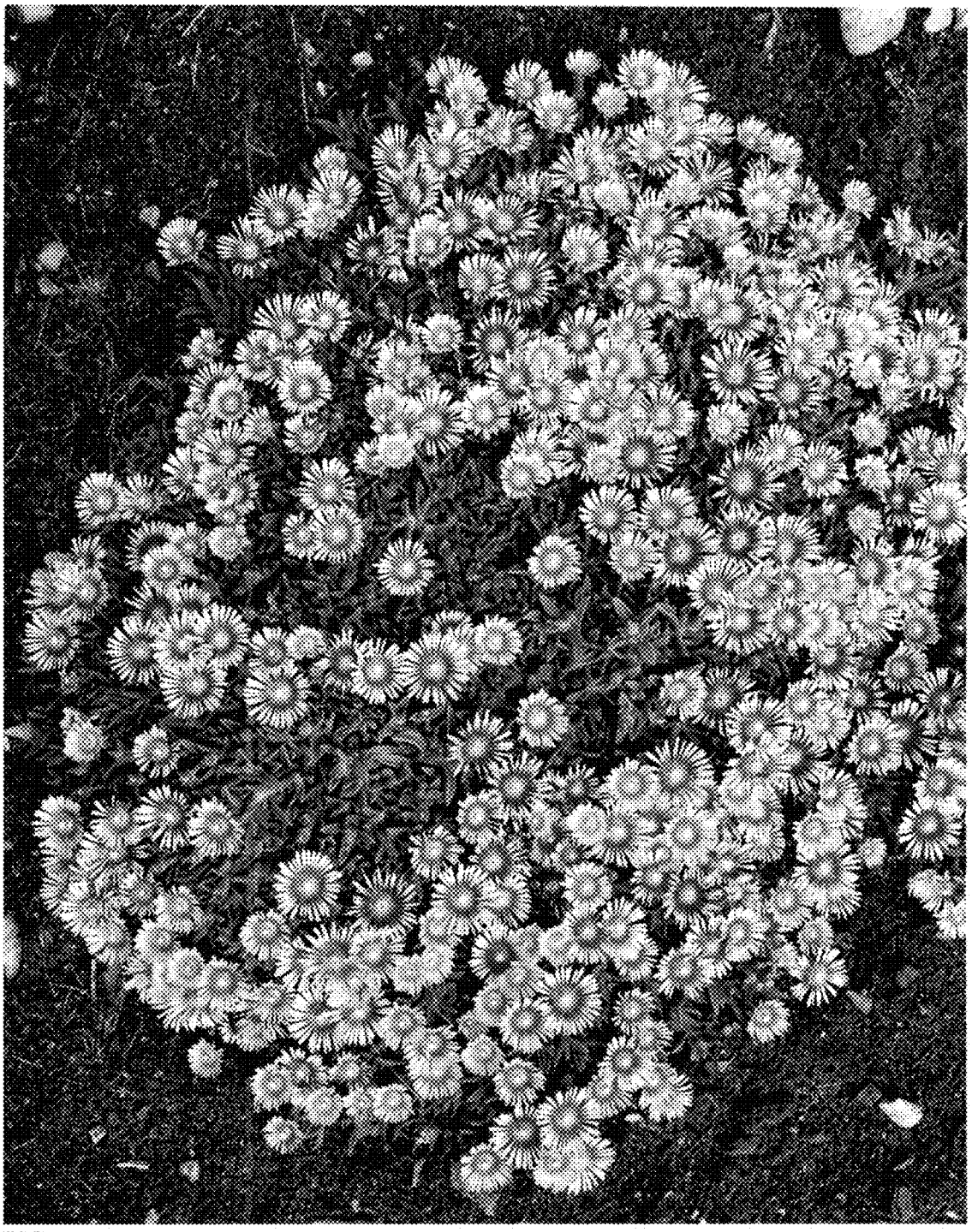
FIG. 1 shows the top-view habit of a two-year-old plant in early flowering.
Figure 2:
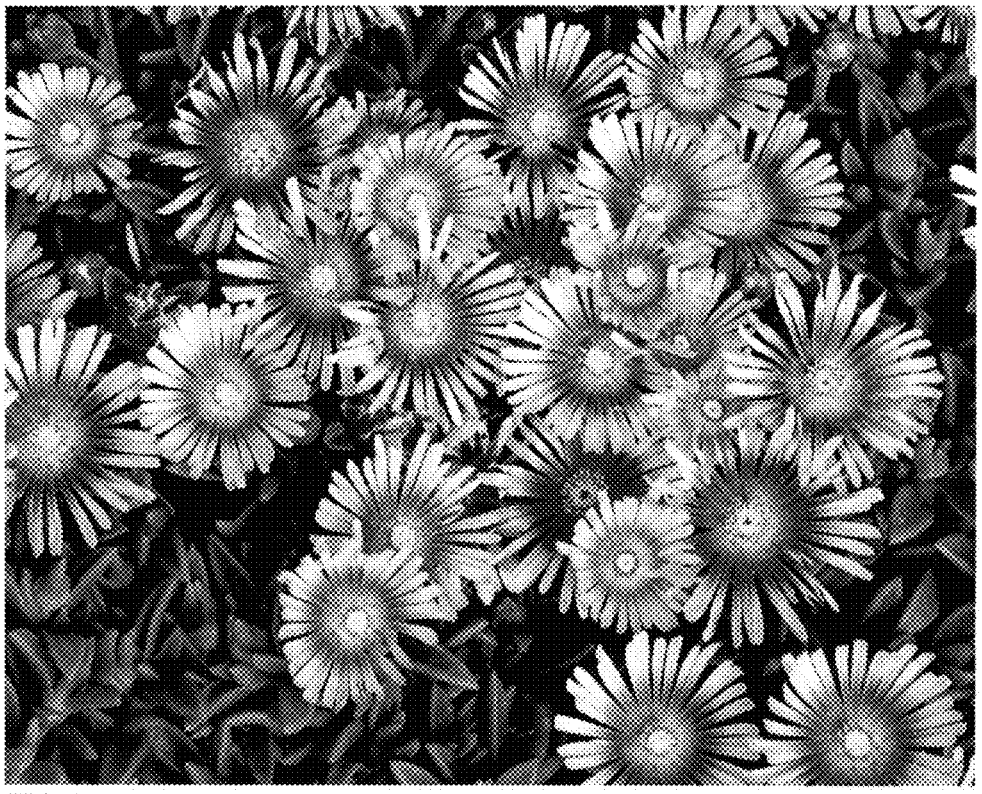
FIG. 2 shows a close-up of the flowers and young buds of a two-year-old plant.
Figure 3:
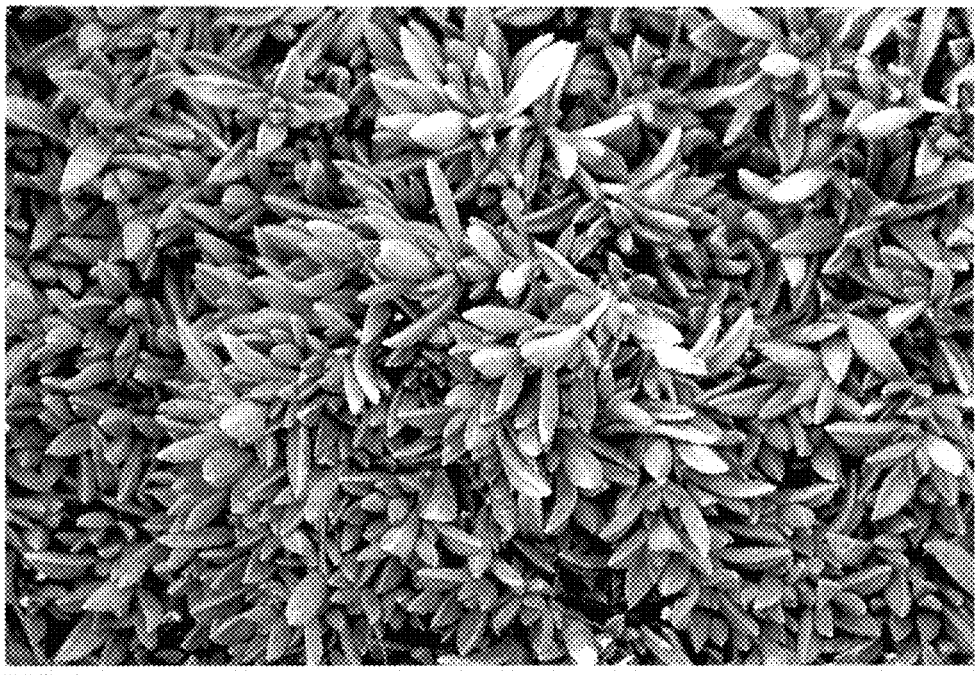
FIG. 3 shows a close-up of the winter foliage of a two-year-old plant.

The following is a detailed description of two-year-old plants of the new cultivar grown outdoors in a full sun display garden with supplemental water and fertilizer as needed at a wholesale nursery in Zeeland, Michigan. No plant growth regulators have been used. Plants of the new cultivar have not been tested under all possible conditions. The phenotype may vary with changes in the environment, climate, and cultural conditions without a change in the genotype. The color reference is in accordance with the 2015 edition of The Royal Horticultural Society Colour Chart except where general color dictionary terms are used.

Botanical designation: *Delosperma* hybrid.

Cultivar denomination: 'Pink Radiance'.

Parentage: The female parent is 'P001S'; the male parent is 'Psfave'.

Asexual propagation: Terminal vegetative cuttings.

Root description: Thin, fibrous, freely branching; color depending on soil matrix, nearest RHS 192D.

Habit: Low sprawling mound; freely-branching; winter-hardy perennial; to about 45 cm wide and 9 cm tall.

Foliage: Opposite; linear; succulent; with acute apex; truncate partially clasping base; entire margins; slightly concavo-convex; adaxial and abaxial surface glandular and slightly lustrous; to about 26 mm long, 8 mm wide slightly distal to center and 3.5 mm thick.

Leaf color: Adaxial and abaxial young between RHS 138B and RHS 138A, adaxial and abaxial mature nearest RHS NN137C; late fall, winter, and early spring color with direct sun exposure between RHS 182C and RHS N186C, portions protected from direct sun variably between RHS 147B and between RHS 146D and RHS 145A.

Stem: Stolon; cylindrical; succulent, and slightly lustrous and glandular distally, matte and more dried proximally; glabrous; to about 9 to 11 cm long and 3 mm diameter; branching at nodes.

Venation: Veins not distinguishable from leaf.

Stem color: Proximally between RHS 161A and RHS 164C, distally between RHS 146D and RHS 145C.

Nodes: Average about 3 mm thick; average about 3 mm diameter; internode distance about 10 mm apart, greater distances distally and shorter at stem base; node color same as surrounding stem.

Branches: To about 11 cm long and 2.5 mm diameter at base; color proximally between RHS 161A and RHS 164C, distally between RHS 146D and RHS 145C.

Petiole: Sessile.

Inflorescence: Single; radial; complete; perfect; actinomorphic; with up to 3 flowers per node.

Flower bud: Globose becoming cylindrical prior to petals opening flat; upright; to about 17 mm tall, 10 mm diameter at apex, and 9 mm diameter at calyx; petal color variable nearest RHS 72D and between RHS 75C and RHS 75D; sepals nearest RHS 138A.

Bloom period: Beginning late May and continuing sparsely into fall in Zeeland, Michigan.

Inflorescence lasting: Two to three days in fully open state.

Individual flower size: To about 40 mm across, 14 mm deep; upwardly.

Petals: To about 38 per flower; linear; apex emarginate with one to two notches about 0.5 mm deep; base truncate; margin entire; strongly lustrous adaxial and abaxial; slightly arcuate downwardly; to about 19 mm long and 2.7 mm across toward apex.

Petal color: When first open adaxial proximal one-third between RHS N78C and RHS N78B, distal two-thirds between RHS 75D and RHS 76D; when first open abaxial proximal one-third nearest N78D, distal margins nearest RHS 76D, and center between RHS N78C and RHS N78B; when mature adaxial proximal one-third nearest 72B and distal two-thirds nearest RHS 75D; when mature abaxial nearest RHS 72B in the proximal one-half transitioning distally to between RHS 76C and RHS 76D along margins and the center between RHS 72B and RHS 72C.

Petaloids: About 36 to 40 per flower; linear; narrowly acute apex; truncate base; entire margin; to about 7 mm long and 0.5 mm across, decreasing in size toward center.

Petaloid color: Adaxial and abaxial between RHS N78C and N78B.

Sepal: Five; deltoid; with acute apex and truncate base; margin entire; adaxial and abaxial glabrous and slightly asperous; sarcous; in a single whorl; size variable, from 10 mm long and 5 mm wide a base to 6 mm long and 4 mm wide at base; short sepals with a 1 mm wide transparent papery margin.

Sepal color: Adaxial nearest RHS 137A and abaxial nearest RHS 137B with papery margins between RHS 158D and RHS 161D.

Pedicel: Cylindrical; asperous; sarcous; to about 16 mm long and 3 mm diameter at base.

Pedicel color: Between RHS 146D and RHS 145B.

Gynoecium: Pentamerous; to about 7 mm long.

Pistil: Five; highly reduced, stigma and style indistinguishable; with stigmatic papillae; conical; to about 4 mm long and 1.5 mm across; color nearest RHS 146D.

Androecium: Quantity about 95 to 120.

*Filament.*—95 to 120; cylindrical; mostly straight; glabrous in exterior position filaments, puberulent in distal 1 mm on interior filaments; lustrous; to 5 mm long and 0.3 mm diameter; color variable, base nearest RHS 76D, distally on exterior filaments between RHS 77B and RHS 77A, and distally on interior filaments nearest RHS 77C.

*Anther.*—Elliptical; to about 1 mm long and 0.5 mm across; color nearest RHS 8C.

*Pollen.*—Abundant; color between RHS 8C and RHS 8B.

Fruit: Penta-dehiscent capsule; to about 9 mm across and 7 mm tall; color nearest RHS 161C when mature.

Seed: To about 85 per flower; ellipsoidal; glabrous; about 0.7 mm long and 0.5 mm across; color variable, nearest RHS N199C, and between RHS 164B and RHS N199C.

Disease resistance: The new plant has not been observed to demonstrate either resistance or susceptibility to diseases and pests that might commonly be found on *Delosperma*.

Growth: The new plant grows best with good drainage and has been shown to be hardy to at least USDA Zones 6 through 10.

I claim:

1. A new and distinct cultivar of *Delosperma* plant named 'Pink Radiance' as herein illustrated and described.

* * * * *